United States Patent
Liu et al.

(10) Patent No.: US 9,795,690 B2
(45) Date of Patent: Oct. 24, 2017

(54) THERAPEUTIC MIRNAS FOR TREATING HEART AND SKELETAL MUSCLE DISEASES

(71) Applicant: UNIVERSITY OF HOUSTON, Houston, TX (US)

(72) Inventors: Yu Liu, Houston, TX (US); Robert Schwartz, Houston, TX (US); Xiaopeng Shen, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 15/215,169

(22) Filed: Jul. 20, 2016

(65) Prior Publication Data
US 2016/0317680 A1 Nov. 3, 2016

Related U.S. Application Data

(62) Division of application No. 14/680,785, filed on Apr. 7, 2015, now Pat. No. 9,439,924.

(60) Provisional application No. 61/977,378, filed on Apr. 9, 2014.

(51) Int. Cl.
| | |
|---|---|
| *A61K 48/00* | (2006.01) |
| *A61K 31/7105* | (2006.01) |
| *A61K 45/06* | (2006.01) |
| *C12N 5/077* | (2010.01) |
| *C12N 15/00* | (2006.01) |
| *A61K 9/00* | (2006.01) |
| *A61K 9/14* | (2006.01) |
| *C12N 7/00* | (2006.01) |
| *C12N 15/11* | (2006.01) |

(52) U.S. Cl.
CPC ........ *A61K 48/0058* (2013.01); *A61K 9/0019* (2013.01); *A61K 9/14* (2013.01); *A61K 31/7105* (2013.01); *A61K 45/06* (2013.01); *A61K 48/00* (2013.01); *A61K 48/0025* (2013.01); *A61K 48/0075* (2013.01); *A61K 48/0083* (2013.01); *C12N 5/0657* (2013.01); *C12N 7/00* (2013.01); *C12N 15/00* (2013.01); *C12N 15/111* (2013.01); *C12N 2310/141* (2013.01); *C12N 2320/30* (2013.01); *C12N 2501/65* (2013.01); *C12N 2506/02* (2013.01); *C12N 2710/10043* (2013.01); *C12N 2740/10043* (2013.01)

(58) Field of Classification Search
CPC .................................................... A61K 48/00
See application file for complete search history.

(56) References Cited

U.S. PATENT DOCUMENTS

| | | |
|---|---|---|
| 2008/0213177 A1 | 9/2008 | Rademacher et al. |
| 2010/0310521 A1 | 12/2010 | Fechner et al. |
| 2013/0017176 A1 | 1/2013 | Hosoda et al. |
| 2014/0155459 A1* | 6/2014 | Chun ................. C12N 15/1136 514/44 A |

FOREIGN PATENT DOCUMENTS

WO   WO 2013/057527 A2   4/2013

OTHER PUBLICATIONS

Zhang et al. (J. Controlled Release 172 (2013): 962-974).*
(see Ghosh et al. J Clinical Investigation 2010: 4141-4154).*
Chen J., et al., mir-17-92 cluster is required for and sufficient to induce cardiomyocyte proliferation in postnatal and adult hearts. *Circ Res*, 2013. 112(12): p. 1557-1566.
Cui Y, et al. "miR-503 represses CUG-binding protein 1 translation by recruiting CUGBP1 mRNA to processing bodies." *Mol. Boil. Cell* (Jan. 1, 2012), vol. 23, No. 1, pp. 151-162, abstract, p. 152, col. 1, para 3, col. 2, para 3, Fig 2B.
Fan D, et al. "Cardiac fibroblasts, fibrosis and extracellular matrix remodeling in heart disease." *Fibrogenesis& Tissue Repair 2012*, vol. 5, No. 15, pp. 1-13, abstract, p. 4, col. 1 para 2, Fig. 1.
Gamez, B., et al., "MicroRNA-322 (miR-322) and its target protein Tob2 modulate Osterix (Osx) mRNA stability." *J Biol Chem*, 2013. 288(20): p. 14264-14275.
Qian L., et al., "In vivo reprogramming of murine cardiac fibroblasts into induced cardiomyocytes". *Nature*, 2012. 485(7400): p. 593-598.
Sarkar S, et al. "MiR-322/424 and -503 are induced during Muscle Differentiation and promote cell cycle quiescence and differentiation by down-regulation of Cdc25A." *Mol Biol Cell*. (Jul. 1, 2010) vol. 21, No. 13, pp. 2138-2139, abstract, p. 2139, col. 2, para 5, p. 2140, col. 2, para 1-3, p. 2141, col. 1, para 1, Fig. 1.
Song K et al. "Heart repair by reprogramming non-myocytes with cardiac transcription factors." *Nature*. (2012), 485(7400):599-604.
Wang J., et al., "Bmp signaling regulates myocardial differentiation from cardiac progenitors through a MicroRNA-mediated mechanism." *Dev Cell*, 2010. 19(6): p. 903-912.
PCT Search Report and Written Opinion issued in International Application No. PCT/US2015/024745, mailed Aug. 28, 2015.
U.S. Non-Final Office Action issued in U.S. Appl. No. 14/680,785, mailed Feb. 11, 2016.

* cited by examiner

*Primary Examiner* — Kimberly Chong
(74) *Attorney, Agent, or Firm* — Parker Highlander PLLC

(57) ABSTRACT

The present disclosure describes the role for miR-322(424)/503 in the differentiation of cardiac precursor cells. Thus, the use of these molecules in the programming of resident stem/progenitor cells into cardiomyocytes, both in vitro and in vivo. Such methods find particular use in the treatment of patients post-myocardial infarction to prevent or limit scarring and to promote myocardial repair.

19 Claims, 3 Drawing Sheets
(3 of 3 Drawing Sheet(s) Filed in Color)

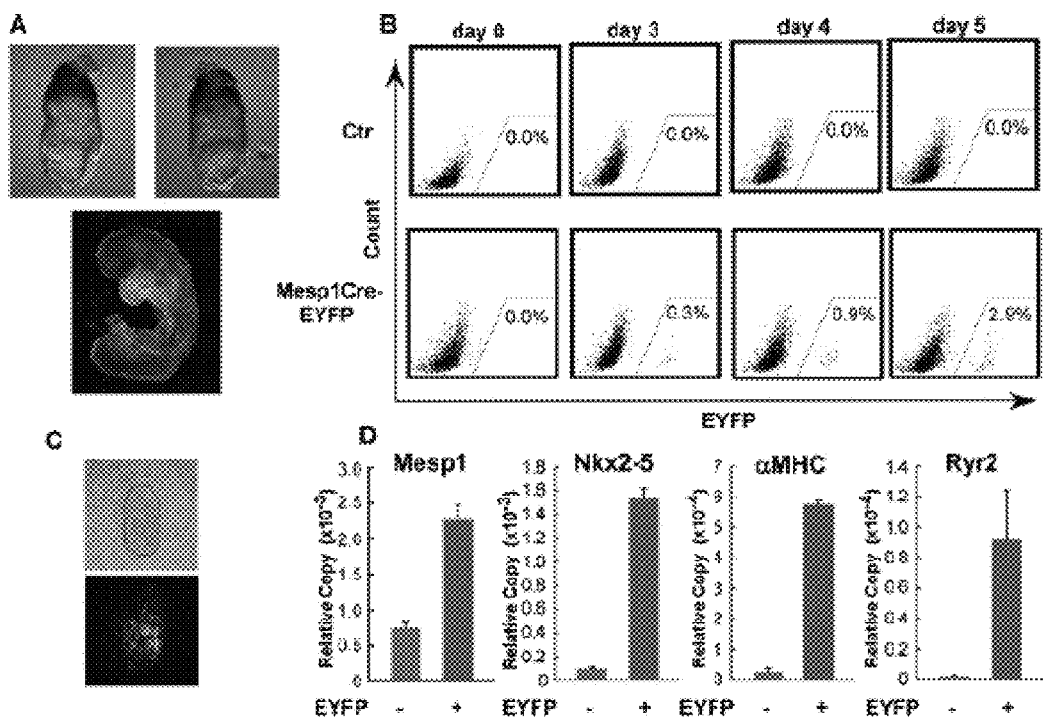
FIGS. 1A-D
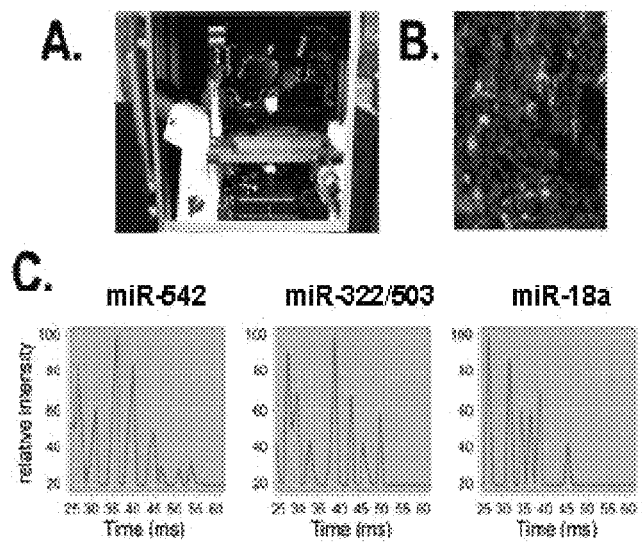
FIGS. 2A-C

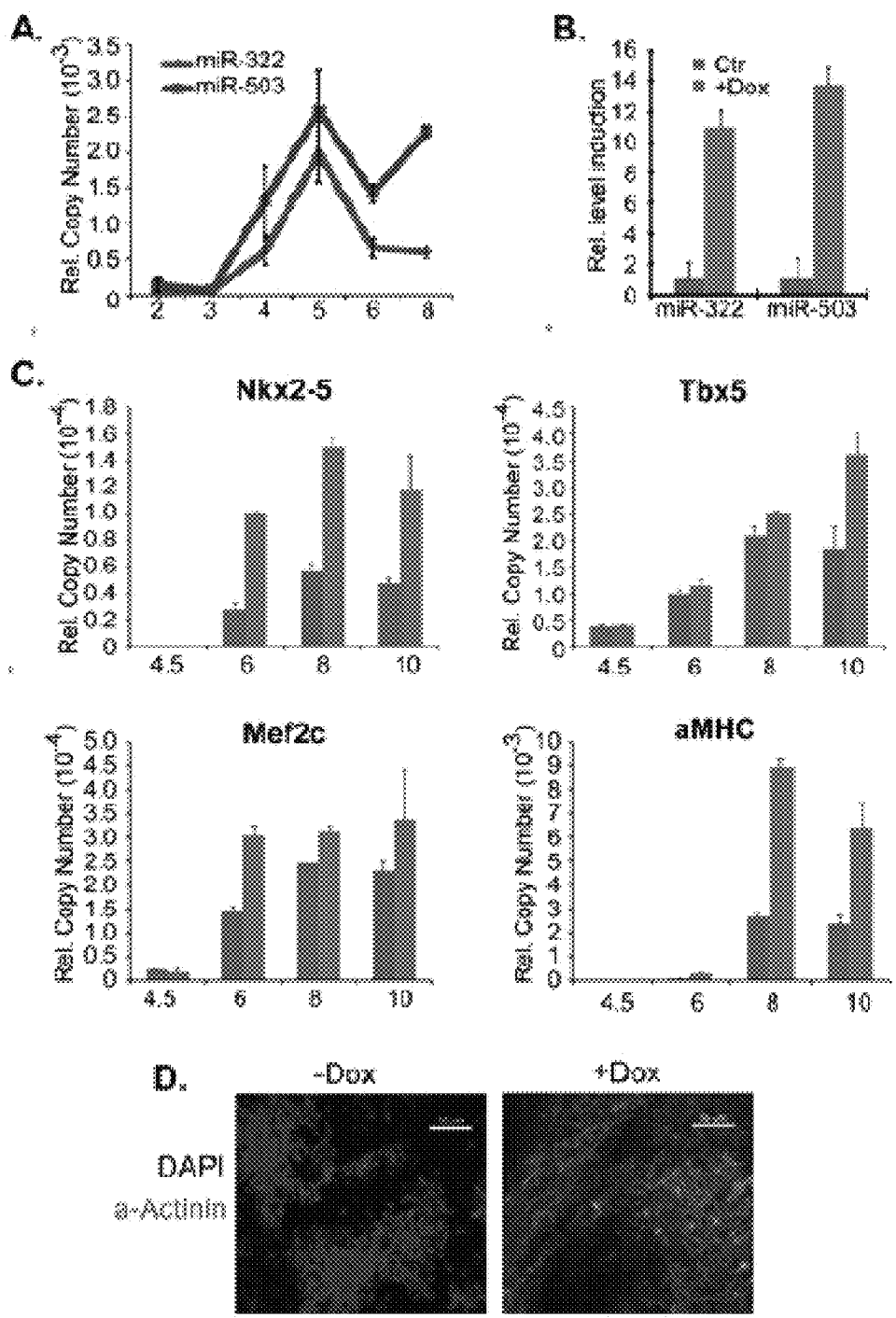
FIGS. 3A-D

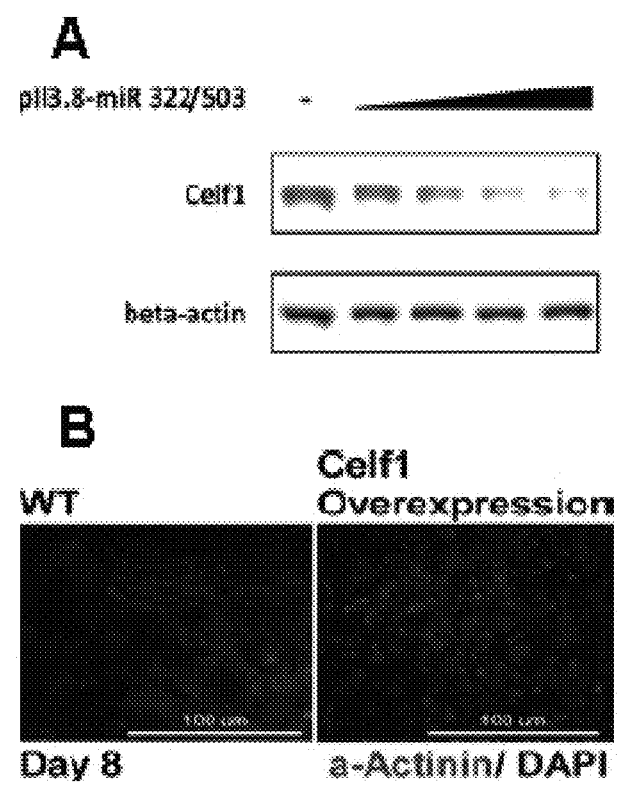
FIGS. 4A-B
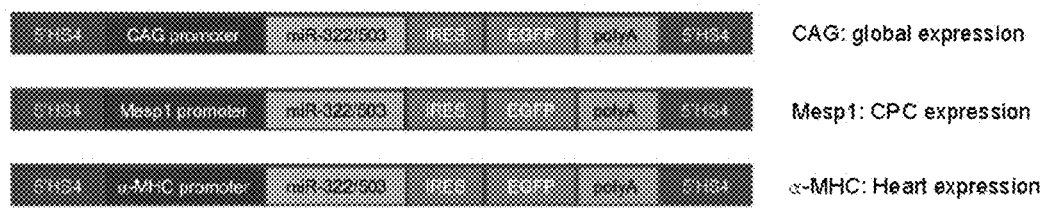
FIG. 5

THERAPEUTIC MIRNAS FOR TREATING HEART AND SKELETAL MUSCLE DISEASES

This application is a divisional of U.S. application Ser. No. 14/680,785 filed Apr. 7, 2015, which claims benefit of priority to U.S. Provisional Application Ser. No. 61/977,378, filed Apr. 9, 2014, the entire contents of each of the above-disclosures is hereby incorporated by reference.

Pursuant to 37 C.F.R. 1.821(c), a sequence listing is submitted herewith as an ASCII compliant text file named "UHOU.P0006US.D1_ST25.txt", created on Jul. 13, 2016 and having a size of ~4 kilobytes. The content of the aforementioned file is hereby incorporated by reference in its entirety.

BACKGROUND

1. Field

The present disclosure relates generally to the fields of cardiology, developmental biology and molecular biology. More particularly, it concerns gene regulation and cellular physiology in cardiomyocytes and skeletal muscle cells. Specifically, the disclosure relates to the use of an miRNA to reprogram cardiac fibroblasts into cardiomyocytes and the use of such miRNA in the prevention of scarring and repair in post-myocardial infarction, and in treating myotonic dystrophy, muscular dystrophy and muscle degenerative diseases.

2. Description of Related Art

Heart failure is one of the leading causes of death in the United States. Because human hearts lack regenerative capacity, cardiomyocyte loss due to a variety of reasons eventually results in loss of pump function and heart failure. Heart transplantation is a valid cure but limited by the availability of donors. This situation calls for approaches to help cardiomyocyte regeneration after injury.

Cell replacement therapy is a focus area in new approaches for treating heart failure. Over the years, peripheral blood, bone marrow cells, skeletal muscle, adipose and ES/iPS-derived cells have been used in efforts to rescue injured hearts, in hope that these cells can trans-differentiate or differentiate into cardiomyocytes (Garbern and Lee, 2013). Though a functional improvement is often seen, it is hardly attributed to new cardiac muscle formation, but conditioning of the microenvironment.

More recently, Olson's and Srivastava's groups independently demonstrated 3-4 transcription factors can directly convert cardiac fibroblasts into cardiomyocytes in vivo, and improve recovering after ischemic heart injury (Qian et al., 2012 and Song et al., 2012). These efforts have laid a foundation for further developing similar reprogramming-based regimens. Among remaining challenges, safe and effective delivering of several transcription factors is still difficult.

SUMMARY

Thus, in accordance with the present disclosure, there is provided a method of a method of programming a cell into cardiac fibroblast comprising contacting said cell with miR-322/424 and/or miR-503, as well pri-miRNAs and pre-miRNAs thereof. The cell may be a residential embryonic stem cell or a residential cardiac progenitor cell. The miR-322/424 and/or miR-503 may be delivered in a lipid delivery vehicle, or in a nanoparticle. Contacting may comprise delivering an miR-322/424 and/or miR-503 expression cassette to said cell, such as one is comprised in a replicable vector, including a viral vector (e.g., adenoviral vector or retroviral vector), or a non-viral vector (e.g., on disposed in a lipid delivery vehicle or a nanoparticle). The expression cassette may comprises a global promoter, a cardiac mesoderm promoter or a cardiomyocyte promoter. The miR-322/424 and/or miR-503 may be contacted with said cell more than once. Celf1 expression in said cell may be reduced 50%, 75%, 80%, 85%, 90% or 95% as compared to an untreated cell.

In another method, there is provided a method of treating a subject having suffered a myocardial infarct (MI) comprising administering to said subject miR-322/424 and/or miR-503, as well pri-miRNAs and pre-miRNAs thereof. The miR-322/424 and/or miR-503 may be administered in a lipid delivery vehicle or a nanoparticle. Administering may comprise delivering an miR-322/424 and/or miR-503 expression cassette to said cell. The expression cassette may be comprised in a replicable vector, such as a viral vector (e.g., adenoviral vector or retroviral vector), or a non-viral vector (e.g., on disposed in a lipid delivery vehicle or a nanoparticle). The expression cassette may comprise a global promoter, a cardiac mesoderm promoter or a cardiomyocyte promoter. The miR-322/424 and/or miR-503 may be administered more than once, such as 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times. The expression cassette may be delivered daily. The miR-322/424 and/or miR-503 may be delivered intracardiac injection. The subject may be further administered oxygen, aspirin, nitroglycerin, percutaneous coronary intervention, and/or a fibrinolytic. The miR-322/424 and/or miR-503 may be targeted to a residential embryonic stem cell or a residential cardiac progenitor cell.

In yet other embodiments, there are provided:

a method preventing or delaying development of cardiac hypertrophy or heart failure in a subject having suffered a myocardial infarct (MI) comprising providing to said subject miR-322/424 and/or miR-503, as well pri-miRNAs and pre-miRNAs thereof.

a method of reducing decrease in exercise tolerance of a subject having suffered a myocardial infarction comprising administering to said subject miR-322/424 and/or miR-503, as well pri-miRNAs and pre-miRNAs thereof.

a method of reducing hospitalization of a subject having suffered a myocardial infarction comprising administering to said subject miR-322/424 and/or miR-503, as well pri-miRNAs and pre-miRNAs thereof.

a method of improving quality of life of a subject having suffered a myocardial infarction comprising administering to said subject miR-322/424 and/or miR-503, as well pri-miRNAs and pre-miRNAs thereof.

a method of decreasing morbidity of a subject having suffered a myocardial infarction comprising administering to said subject miR-322/424 and/or miR-503, as well pri-miRNAs and pre-miRNAs thereof.

a method of decreasing mortality of a subject having suffered a myocardial infarction comprising administering to said subject miR-322/424 and/or miR-503, as well pri-miRNAs and pre-miRNAs thereof.

For each of the foregoing embodiments, the miR-322/424 and/or miR-503 is administered in a lipid delivery vehicle or a nanoparticle. Administering may comprise delivering an miR-322/424 and/or miR-503 expression cassette to said cell, such as a replicable vector like a viral vector (e.g., adenoviral vector or retroviral vector), or a non-viral vector (e.g., on disposed in a lipid delivery vehicle or a nanoparticle). The expression cassette may comprise a muscle specific promoter. The miR-322/424 and/or miR-503 may be administered more than once, such as 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times. The expression cassette may be delivered daily.

In still yet another embodiment, there is provided a method of treating a subject having a muscle degenerative disease comprising administering to said subject miR-322/424 and/or miR-503. The muscle degenerative disease may be myotonic dystrophy 1 or muscular dystrophy. The miR-322/424 and/or miR-503 is administered in a lipid delivery vehicle or a nanoparticle. Administering may comprise delivering an miR-322/424 and/or miR-503 expression cassette to said cell, such as a replicable vector like a viral vector (e.g., adenoviral vector or retroviral vector), or a non-viral vector (e.g., on disposed in a lipid delivery vehicle or a nanoparticle). The expression cassette may comprise a muscle specific promoter. The miR-322/424 and/or miR-503 may be administered more than once, such as 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times. The expression cassette may be delivered daily.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIGS. 1A-D. (FIG. 1A) Tracing the Mesp1 in developing embryos. Top: E7.5; Bottom:E9.5. (FIG. 1B) Tracing the Mesp1-lineage cells during ES cell differentiation by FACS. (FIG. 1C) Spontaneous beating (top circled area) overlaps with Mesp1Cre-driven YFP signal (bottom) at day 8 of EB culture. (FIG. 1D) Cardiac genes are enriched in the YFP+ population.

FIGS. 2A-C. (FIG. 2A) The IC-200 high-throughput microscopy manufactured by Vala Scineces. (FIG. 2B) Gating by DAPI staining for the identification of individual cells and Fluo-4 calcium signals. (FIG. 2C) Examples of early excitability of cardiac progenitor cells harboring ectopic miRNAs.

FIGS. 3A-D. (FIG. 3A) Expression profile of miR-322 and 503 during ES cell differentiation. (FIG. 3B) induction of miR-322 and 503 expression by doxycycline. (FIG. 3C) Dox-Induced miR-322/503 led to precocious cardiac gene induction. (FIG. 3D) Dox-induced miR-322/503 triggered precocious expression of a-Actinin.

FIGS. 4A-B. (FIG. 4A) miR-322/503 inhibited Celf1 expression. (FIG. 4B) Ectopic expression of Celf1 represses cardiac differentiation.

FIG. 5. Schematic maps of transgenic constructs.

DETAILED DESCRIPTION OF ILLUSTRATIVE EMBODIMENTS

Heart failure is one of the leading causes of morbidity and mortality in the world. In the U.S. alone, estimates indicate that 3 million people are currently living with cardiomyopathy and another 400,000 are diagnosed on a yearly basis. Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars.

One particularly severe manifestation of heart disease is myocardial infarction (MI). Typically, MI results from an acute thrombocytic coronary occlusion that occurs in a coronary artery as a result of atherosclerosis and causes myocardial cell death, i.e., an infarct. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic. Cardiac hypertrophy is an adaptive response of the heart to virtually all forms of cardiac disease, including myocardial infarction. While the hypertrophic response is initially a compensatory mechanism that augments cardiac output, sustained hypertrophy can lead to DCM, heart failure, and sudden death. In the United States, approximately half a million individuals are diagnosed with heart failure each year, with a mortality rate approaching 50%.

Treatment with pharmacological agents still represents the primary mechanism for reducing or eliminating the manifestations of heart failure, including those resulting from MIs. Diuretics constitute the first line of treatment for mild-to-moderate heart failure. Unfortunately, many of the commonly used diuretics (e.g., the thiazides) have numerous adverse effects. For example, certain diuretics may increase serum cholesterol and triglycerides. Moreover, diuretics are generally ineffective for patients suffering from severe heart failure. If diuretics are ineffective, vasodilatory agents may be used; the angiotensin converting (ACE) inhibitors (e.g., enalopril and lisinopril) not only provide symptomatic relief, they also have been reported to decrease mortality (Young et al., 1989). Again, however, the ACE inhibitors are associated with adverse effects that result in their being contraindicated in patients with certain disease states (e.g., renal artery stenosis). Similarly, inotropic agent therapy (i.e., a drug that improves cardiac output by increasing the force of myocardial muscle contraction) is associated with a panoply of adverse reactions, including gastrointestinal problems and central nervous system dysfunction.

Thus, the currently used pharmacological agents have severe shortcomings in particular patient populations. More importantly, none of these agents are capable of reversing the damage caused by an acute coronary event, and thus are only compensatory, and only then to a certain degree. The prognosis for patients with DCM is variable, and depends upon the degree of ventricular dysfunction, with the majority of deaths occurring within five years of diagnosis.

Micro RNAs (miRNAs) are powerful regulators of gene expression and biological processes. They can be synthesized, conjugated to vehicles, delivered locally and systemically thus hold great pharmaceutical value (Soifer et al., 2007). The inventors have identified miRNAs sitting high on the cardiac program hierarchy, by tracking the descendants of Mesp1-expressing progenitor cells. Compared to the current pool of cardiac regulatory miRNAs in the literature, these new miRNAs may be suitable to drive a progenitor cell type which is capable to proliferate and differentiate into multiple cooperative cell types for concerted therapy effect.

The inventors present evidence here that miR-322(424)/503 are major regulators of the early cardiac program and can be used to regenerate major cardiac cells after ischemic injury. This cluster was identified by a screening of 20 cardiac progenitor cell (CPC)-enriched miRNAs for their ability to drive a cardiac program in embryonic stem cells. Their preliminary results support the notion that miR-322/503 are novel regulators of the cardiac program: (1) miR-322(424)/503 had the highest fold-enrichment in Mesp1-expressing cells. (2); it was highly enriched in heart and skeletal muscles; (3) it induced precocious appearance of cardiomyocytes when ectopically expressed to mimic the natural course of expression; and (4) miR-322(424)/503 targeted factors chiefly expressed in neural lineages. Application of miR-322(424)/503 as therapeutic agents in the treatment of heart and muscle disease are disclosed in detail below.

I. Mirnas miRNAs are a group of short non-coding RNAs. miRNAs are regulators in almost all biological process, including cell fate decisions (Ambros 2004). miRNAs are first transcribed as long transcripts—pre-miRNAs, and then processed by Drosha/DGCR8 and Dicer to be ~20-22 nucleotide oligo RNAs. The oligo RNAs are then load onto the RNA-induced silencing complex (RISC) to form mature gene-silencing complexes, which induce target mRNA degradation or transcription repression. Each miRNA targets hundreds of mRNAs, making miRNAs crucial regulators in the network of biological pathways. Because of the chemical nature of miRNAs, they can be synthesized, conjugated, locally or globally administered, thus having a direct route toward therapeutic uses.

miRNAs have important roles in regulating development of the cardiovascular system (Small and Olson, 2011). Conditional deletion of Dicer, an essential component for miRNA maturation, led to E12.5 lethality with abnormal heart morphogenesis (Bernstein et al., 2003) miR-1, 133, 208, and 499 are specifically expressed in cardiac and skeletal muscles. Genetic analyses have shown that they play critical roles for myocyte formation or function (van Rooij et al., 2009, van Rooij et al., 2007, Liu et al., 2008, Liu et al., 2007 and Yang et al., 2007). The miR-143/145 cluster was enriched in vascular smooth muscle cells, and they appeared to regulate SMC fate and plasticity (Xin et al., 2009). Despite the proven roles, these miRNAs have a relative late onset, corresponding to the expression of cardiac transcription factors (Nkx2-5, Tbx5, Mef2c, etc.) and structural genes (aMHC, Ryr2, etc.). Upstream miRNAs, corresponding to the expression of cardiac mesoderm markers including Mesp1, Flk1 and Pdgfra, are currently unknown.

miR-322/503 cluster, consisting of miR-322 and miR-503, is encoded by a locus on the X chromosome. miR-322 and miR-503 are reported to play important roles in differentiation processes. miR-322, down-regulated by BMP2, promotes osteogenesis (Gamez et al., 2013) miR-322 and miR-503 promote muscles differentiation and inhibit cell cycle by targeting Cdc25A (Sarkar et al., 2010). miR-322 and miR-503 are the top two miRNAs enriched in Mesp1-positive progenitor cells, 25-times more than their expressions in Mesp1 negative cells by RNA sequencing. miR-322 and miR-503 display peaks at day 5 ES cell differentiation in a standard differentiation protocol.

The sequence for miR-322 is shown below:

```
                                        [SEQ ID NO: 1]
cagcagcaauucauguuuugga
```

The sequence for miR-424, which differs in sequences from miR-322 by a single nucleotide, is shown below:

```
                                        [SEQ ID NO: 2]
cagcagcaauucauguuuugaa
```

The sequence for human miR-503 is shown below:

```
                                        [SEQ ID NO: 3]
uagcagcgggaacaguucugcag
```

Also contemplated for use according to the present disclosure are pri-miRNAs and pre-miRNAs thereof, orthologs from other species, as well as paralogs having similar sequences, some of which are shown below:

```
Rat miR, rno-miR-322,
                                        [SEQ ID NO: 4]
cagcagcaauucauguuuugga Cricetulus griseus, Cgr-miR-322,
                                        [SEQ ID NO: 5]
cagcagcaauucauguuuugg Macaca mulatta, mml-miR-424,
                                        [SEQ ID NO: 6]
cagcagcaauucauguuuugaa Pan troglodytes, ptr-mir-424,
                                        [SEQ ID NO: 7]
cagcagcaauucauguuuugaa Bos Taurus, bta-mir-424,
                                        [SEQ ID NO: 8]
cagcagcaauucauguuuuga Equus caballus, eca-mir-424,
                                        [SEQ ID NO: 9]
cagcagcaauucauguuuugaa Pongo pygmaeus, ppy-mir-424,
                                        [SEQ ID NO: 10]
cagcagcaauucauguuuugaa Gorilla gorilla, ggo-mir-424,
                                        [SEQ ID NO: 11]
cagcagcaauucauguuuuga Mouse, mmu-mir-503,
```

-continued uagcagcgggaacaguacugcag [SEQ ID NO: 12]

Rattus norvegicus, rno-mir-503,
uagcagcgggaacaguacugcag [SEQ ID NO: 13]

Macaca mulatta, mml-mir-503,
uagcagcgggaacaguucugcag [SEQ ID NO: 14]

Canis familiaris, cfa-mir-503,
uagcagcgggaacaguacug [SEQ ID NO: 15]

Pan troglodytes, ptr-mir-503,
uagcagcgggaacaguucugcag [SEQ ID NO: 16]

Sus scrofa, ssc-mir-503,
uagcagcgggaacaguacugcag [SEQ ID NO: 17]

Equus caballus, eca-mir-503,
uagcagcgggaacaguacugcag [SEQ ID NO: 18]

Pongo pygmaeus, ppy-mir-503,
uagcagcgggaacaguucugcag [SEQ ID NO: 19]

Gorilla gorilla, ggo-mir-503,
uagcagcgggaacaguucugcag [SEQ ID NO: 20]

Bos Taurus, bta-mir-503,
uagcagcgggaacaguacug [SEQ ID NO: 21]

II. Delivery Vehicles

A. Lipid Delivery Vehicles

In certain embodiments, the use of lipid delivery vehicles (e.g., liposomes) is contemplated for the formulation and administration of the miRNAs disclosed herein, or expression cassettes coding therefor. The formation and use of liposomes is generally known to those of skill in the art, and is also described below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200-500 Å, containing an aqueous solution in the core.

The following information can also be utilized in generating liposomal formulations. Phospholipids can form a variety of structures other than liposomes when dispersed in water, depending on the molar ratio of lipid to water. At low ratios the liposome is the recommended structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs. Liposomes may also be characterized by the type of lipid the comprise—positively charged, negatively charged or neutral lipids.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one can operate at the same time.

B. Nanoparticles miRNAs have the intrinsic advantage as a therapeutic agents over other molecules such as DNA and protein. The targeted in vivo delivery of them, however, faces challenges including limited stability in serum, rapid kidney clearance and inefficient cellular uptake. Thus, the inventors contemplate delivery of miRNAs or expression cassettes coding therefor using nanoparticles.

In nanotechnology, a particle is defined as a small object that behaves as a whole unit with respect to its transport and properties. Particles are further classified according to diameter, with those under 1 µm in size being nanoparticles, but more generally between 1 and 100 nanometers in size. Nanoparticles can be made of a variety of different materials—examples include proteins, lipid, polymers and metals. Depending on their composition, synthesis and use, they may carry deliverable molecules on their surface or internally.

A particular gold nanoparticle system has been developed for miRNA delivery: cysteamine-functionalized gold nanoparticles (AuNPs). In two different models, the best formulation of miR1-AuNP10-S-PEG0.5 had the highest payload (10-20 fold higher than lipofection), lowest toxicity (98% of cell viability following treatment), efficient uptake (96% of cells took it), fastest endosomal escape and increased half-lives (at least 5 days)[28]. With changing ratios among miRNA, AuNP10, and PEG (centered on 1 µg miRNA: 10 µg AuNP10: 0.5 µg PEG), one can evaluate payload, cellular uptake, and half-lives. The best formulation is determined as balanced performance in both cell types.

III. Expression Cassettes

As discussed above, in certain embodiments, expression cassettes are employed to express a miRNA, either for subsequent purification and delivery to a cell/subject, or for use directly in a genetic-based delivery approach. Expression requires that appropriate signals be provided in the vectors, and include various regulatory elements such as enhancers/promoters from both viral and mammalian sources that drive expression of the genes of interest in cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

A. Regulatory Elements

Throughout this application, the term "expression cassette" is meant to include any type of genetic construct containing a nucleic acid coding for a gene product in which part or all of the nucleic acid encoding sequence is capable of being transcribed and translated, i.e., is under the control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene. An "expression vector" is meant to include expression cassettes comprised in a genetic construct that is capable of replication, and thus including one or more of origins of replication, transcription termination signals, poly-A regions, selectable markers, and multipurpose cloning sites.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (t k) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

In certain embodiments, viral promotes such as the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized. Further, selection of a promoter that is regulated in response to specific physiologic signals can permit inducible expression of the gene product.

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α₁-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |

TABLE 2-continued

Promoter and/or Enhancer

| Promoter/Enhancer | References |
|---|---|
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |

TABLE 3-continued

Inducible Elements

| Element | Inducer | References |
|---|---|---|
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the α-actin promoter (Moss et al., 1996), the troponin 1 promoter (Bhaysar et al., 1996); the $Na^+/Ca^{2+}$ exchanger promoter (Barnes et al., 1997), the dystrophin promoter (Kimura et al., 1997), the α7 integrin promoter (Ziober and Kramer, 1996), the brain natriuretic peptide promoter (LaPointe et al., 1996) and the αB-crystallin/small heat shock protein promoter (Gopal-Srivastava, 1995), α-myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the disclosure, and any such sequence may be employed such as human growth hormone and SV40 polyadenylation signals. Also contemplated as an element of the expression cassette is a terminator. These elements can serve to enhance message levels and to minimize read through from the cassette into other sequences.

B. Multigene Constructs and IRES

In certain embodiments of the disclosure, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

C. Delivery of Expression Vectors

There are a number of ways in which expression vectors may be introduced into cells. In certain embodiments of the disclosure, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In one system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the disclosure. The adenovirus may be of any of the 42 different known serotypes or subgroups A-F. Adenovirus type 5 of subgroup C is the preferred starting material in order to obtain the conditional replication-defective adenovirus vector for use in the present disclosure. This is because Adenovirus type 5 is a human adenovirus about which a great deal of biochemical and genetic information is known, and it has historically been used for most constructions employing adenovirus as a vector.

As stated above, the typical vector according to the present disclosure is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the disclosure. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present disclosure. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present disclosure. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present disclosure. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, nonspecific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the disclosure, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the disclosure for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present disclosure.

In a further embodiment of the disclosure, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection. A reagent known as Lipofectamine 2000™ is widely used and commercially available.

In certain embodiments of the disclosure, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present disclosure. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

IV. Methods of Treating Myocardial Infarction

As discussed above, the present disclosure provides for new post-MI therapies. In one embodiment of the present disclosure, methods for the treatment of subjects following an MI provides for one or more of the following outcomes as compared to an untreated patient: increased exercise capacity, increased blood ejection volume, decreased left ventricular end diastolic pressure, decreased pulmonary capillary wedge pressure, increased cardiac output, improved cardiac index, decreased pulmonary artery pressures, decreased left ventricular end systolic and diastolic dimensions, and decreased left ventricular wall stress, decreased wall tension and decreased wall thickness-same for right ventricle. In addition, the treatment may prevent progression to cardiac hypertrophy and ultimately heart failure.

Treatment regimens would vary depending on the clinical situation. However, in general, the treatment would begin at a time following an MI when the patient has been stabilized, but before significant cardiac fibroblast mobilization and scarring has begun. The patient may or may not be undergoing one or more other therapies for either prevention or treatment of an MI, or prevention or treatment of MI-related sequelae. This would mean initiating a treatment within about 24, 36, 38, 72, 96 hours of an MI, or within about 5, 6, 7, 8, 9 or 10 days of an MI. The therapy may continue for as long as cardiac fibroblasts would be active within the ischemic zone, such as up to 7 days, 14 days 21 days, 28 days, 1 month, 2 months, 3 months or longer.

A. Combined Therapies

In another embodiment, it is envisioned to use the transcription therapy inhibitor of the present disclosure in combination with other MI and post-MI therapeutic modalities, such as those discussed above. Combinations may be achieved by contacting cardiac cells/patients with a single composition or pharmacological formulation that includes both agents, or by contacting the cell with two distinct compositions or formulations, at the same time, wherein one composition includes the expression construct and the other includes the agent. Alternatively, the therapy using miR322 (424)/503 may precede or follow administration of the other agent(s) by intervals ranging from minutes to weeks. In embodiments where the other agent and miR-322(424)/503 are applied separately to the cardiac cells/patient, one would generally ensure that a significant period of time did not expire between the time of each delivery, such that the agent and miR-322(424)/503 would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either miR-322(424)/503 or the other agent will be desired. In this regard, various combinations may be employed. By way of illustration, where the miRNA is "A" and the other agent is "B," the following permutations based on 3 and 4 total administrations are exemplary:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are likewise contemplated.

B. Standard MI Therapeutic Intervention

Therapies for acute myocardial infarction are designed to restore perfusion as soon as possible to rescue the infracted myocardium. This is typically done by pharmaceutical intervention or by mechanical means, such as percutaneous coronary intervention (PCI) or coronary artery bypass grafting. Recent studies suggest that these treatments are more effective if the following guidelines are followed: <90 min for PCI and <30 min for lytics. Treatmetns outside these windows were associated with increased mortality and significantly increased risk of readmission for acute myocardial infarction or heart failure.

1. Thrombolytic Therapy

Thrombolytic therapy improves survival rates in patients with acute myocardial infarction if administered in a timely fashion in the appropriate group of patients. If PCI capability is not available within 90 minutes, then choice is to administer thrombolytics within 12 hours of onset of symptoms in patients with ST-segment elevation greater than 0.1 mV in 2 or more contiguous ECG leads, new left bundle-branch block (LBBB), or anterior ST depression consistent with posterior infarction. Tissue plasminogen activator (t-PA) is preferred over streptokinase as achieving a higher rate of coronary artery patency; however, the key lies in speed of the delivery.

Aspirin has been shown to decrease mortality and re-infarction rates after myocardial infarction. Again, delivery should be immediate, which should be chewed if possible. The treatment should continues indefinitely in the absence of obvious contraindication, such as a bleeding tendency or an allergy. Clopidogrel may be used as an alternative in cases of a resistance or allergy to aspirin (dose of 300 mg), but a higher dose of clopidogrel may have added benefit.

Platelet glycoprotein (GP) IIb/IIIa-receptor antagonist is another therapy in patients with continuing ischemia or with other high-risk features and to patients in whom a percutaneous coronary intervention (PCI) is planned. Eptifibatide and tirofiban are approved for this use, and abciximab also can be used for 12-24 hours in patients with unstable angina or NSTEMI in whom a PCI is planned within the next 24 hours.

Heparin and other anticoagulant agents have an established role as adjunct agents in patients receiving t-PA, but not in patients receiving streptokinase. Heparin is also indicated in patients undergoing primary angioplasty. Low molecular-weight heparins (LMWHs) have been shown to be superior to UFHs in patients with unstable angina or NSTEMI. Bivalirudin, a direct thrombin inhibitor, has shown promise in STEMI if combined with high-dose clopidogrel.

Nitrates have no apparent impact on mortality rate in patients with ischemic syndromes, but they are useful in symptomatic relief and preload reduction, so much so that all patients with acute myocardial infarction are given nitrates within the first 48 hours of presentation, unless contraindicated (i.e., in RV infarction). Beta-blockers may reduce the rates of reinfarction and recurrent ischemia, and thus are administered to patients with MIs unless a contraindication is present.

ACE inhibitors reduce mortality rates after myocardial infarction and thus are administered as soon as possible as long as no contraindications are and the patient remains stable. ACE inhibitors have the greatest benefit in patients with ventricular dysfunction. Continue ACE inhibitors indefinitely after myocardial infarction. Angiotensin-receptor blockers may be used as an alternative in patients who develop adverse effects, such as a persistent cough, although initial trials need to be confirmed.

2. PCI and Other Surgical Intervention

PCI is the treatment of choice in most patients with STEMI, assuming a door to balloon time of less than 90 minutes. PCI provides greater coronary patency (>96% thrombolysis), lower risk of bleeding, and instant knowledge about the extent of the underlying disease. Studies have shown that primary PCI has a mortality benefit over thrombolytic therapy. The choice of primary PCI should be individualized to each patient's presentation and timing. Primary PCI is also the treatment of choice in patients with cardiogenic shock, patients in whom thrombolysis failed, and those with high risk of bleeding or contraindications to thrombolytic therapy.

Emergent or urgent coronary artery graft bypass surgery is indicated in patients in whom angioplasty fails and in patients who develop mechanical complications such as a VSD, LV, or papillary muscle rupture.

C. Pharmacological Cardiovascular Therapeutic Agents

In addition to the miRNA of the present disclosure, it should be noted that any of the following may be used to develop new therapeutic regimens in combination with the miRNA.

1. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present disclosure, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thryroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8, 11, 14, 17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

2. Antiarteriosclerotics

Non-limiting examples of an antiarteriosclerotic include pyridinol carbamate.

3. Antithrombotic/Fibrinolytic Agents

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

4. Blood Coagulants

In certain embodiments wherein a patient is suffering from a hemmorage or an increased likelyhood of hemmoraging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamine K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

5. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents.

a. Sodium Channel Blockers

Non-limiting examples of sodium channel blockers include Class IA, Class TB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecainide (tambocor).

b. Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (nifedipine-type) calcium antagonist.

e. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyranide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

6. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimefylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative.

Arylethanolamine Derivatives.

Non-limiting examples of arylethanolamine derivatives include amosulalol, bufuralol, dilevalol, labetalol, pronethalol, sotalol and sulfinalol.

Benzothiadiazine Derivatives.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothiazide, hydroflumethiazide, methyclothiazide, meticrane, metolazone, paraflutizide, polythizide, tetrachlormethiazide and trichlormethiazide.

N-carboxyalkyl(peptide/lactam) Derivatives.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives.

Non-limiting examples of dihydropyridine derivatives include amlodipine, felodipine, isradipine, nicardipine, nifedipine, nilvadipine, nisoldipine and nitrendipine.

Guanidine Derivatives.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines.

Non-limiting examples of hydrazines/phthalazines include budralazine, cadralazine, dihydralazine, endralazine, hydracarbazine, hydralazine, pheniprazine, pildralazine and todralazine.

Imidazole Derivatives.

Non-limiting examples of imidazole derivatives include clonidine, lofexidine, phentolamine, tiamenidine and tolonidine.

Quanternary Ammonium Compounds.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives.

Non-limiting examples of reserpine derivatives include bietaserpine, deserpidine, rescinnamine, reserpine and syrosingopine.

Suflonamide Derivatives.

Non-limiting examples of sulfonamide derivatives include ambuside, clopamide, furosemide, indapamide, quinethazone, tripamide and xipamide.

g. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

7. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine administration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyl-theophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-di sulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticrnafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include amrinone (inocor).

d. Antianginal Agents

Antianginal agents may comprise organonitrates, calcium channel blockers, beta blockers and combinations thereof.

Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

D. Surgical Therapeutic Agents

In certain aspects, the secondary therapeutic agent may comprise a surgery of some type, such as PCI. Surgery, and in particular a curative surgery, may be used in conjunction with other therapies, such as the present disclosure and one or more other pharmacologic agents. Such surgical approaches for vascular and cardiovascular diseases and disorders are well known to those of skill in the art, and are described elsewhere in this document.

E. Drug Formulations and Routes for Administration to Patients

Where clinical applications are contemplated, pharmaceutical compositions will be prepared in a form appropriate for the intended application. Generally, this will entail preparing compositions (e.g., miRNA or expression vector)

that are essentially free of pyrogens, as well as other impurities that could be harmful to humans or animals.

One will generally desire to employ appropriate salts and buffers to render drugs, proteins or delivery vectors stable and allow for uptake by target cells. Aqueous compositions of the present disclosure comprise an effective amount of the drug, vector or proteins, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the vectors or cells of the compositions.

The active compositions of the present disclosure may include classic pharmaceutical preparations. Administration of these compositions according to the present disclosure may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

V. EXAMPLES

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Establishing ES Cell Lines to Track Early Cardiac Progenitor Cells.

Given the undisputed importance of Mesp1 in cardiac development, the inventors started with building a system that traces the Mesp1-lineage of cells. Mouse strains Mesp1$^{Cre/+}$ and Rosa26$^{EYFP/EYFP}$ were crossed to produce the genotype Mesp1$^{Cre/+}$:Rosa26$^{EYFP/+}$ FIG. 1A shows the distribution of Mesp1-lineage cells, which were previously determined to be the heart, dorsal aorta and intersomatic vessles (Saga et al., 2000 and Saga et al., 1999). With the conventional blastocyst isolation method, the inventors have established ES cell lines. In a standard embryoid body culture protocol, Mesp1Cre-driven YFP signal starts to appear at day 3 and peaks at day 5. At day 8, YFP signal colocalizes with spontaneous beating areas. Similarly, markers of cardiac development are highly enriched in the YFP(+) population. This cell culture model has several folds of advantage over others that mark/trace cardiac progenitors: (1) Mesp1 is the most specific marker of cardiac progenitors in the earliest stage of cardiac development; (2) Mesp1 knock-in provides the ultimate fidelity; (3) The Cre-loxP system allows the tracing of Mesp1-lineage at ever y stage of cardiac differentiation, despite the transient expression of Mesp1 itself.

miR-322/503 is the Highest Enriched in CPC's and Induce a Cardiac Program in Focused Screening.

Next, the inventors screened the non-coding RNAs selectively enriched in Mesp1-lineage cells by next-generation sequencing. The heart and skeletal muscle specific miRNAs, namely, miR-1, 133, 206, 208, 499 are not among the highly enriched miRNA list, perhaps due to the late onset of these miRNAs. Instead, the inventors have identified many miRNAs with potential early roles in cardiac development. Shown in the following table is two largest clusters enriched in cardiac progenitor cells. Among the list are members of the miR-17-92 family, its paralogs, the 106b-25 family and 106a-363 family, which were shown to promote cardiac progenitor differentiation in mouse embryos (Wang et al., 2010), and promote cardiomyocyte proliferation (Chen et al., 2013).

TABLE 1 miRNA clusters enriched in Mesp1Cre-EYFP positive cells (fold enrichment)

| | |
|---|---|
| miR-322-450 cluster | miR-322 (25.0), miR-503 (25.0), miR-351 (n/a, read 33 vs 0), miR-542 (10.2), miR-450a-2 (16.3), miR-450a-1 (19.3), miR-450b (15.1). |
| miR-17-92 cluster and paralogs | miR-17-92 cluster: mir-17 (7.7), mir-18a (7.0), miR-19a (11.3), mir-20a (6.7), miR-19b-1 (5.0), miR-92a-1 (4.6). miR-106b-25 cluster: miR-106b (6.8), miR-93 (5.5), miR-25 (7.4). miR-106a-363 cluster: miR-106a (5.1), miR-18b (4.8). mir-20b (4.1), miR-19b-2 (6.0), miR-92a-2 (3.3), mir-363 (5.9), |

With the identification of non-coding RNAs highly enriched in Mesp1-lineage cells, the inventors hypothesized that these miRNAs may function through several means to contribute to heart development: (1) inhibit the pluripotency program and other cell lineage programs; (2) induce the Mesp1-lineage; (3) promote the further development of Mesp1-lineage cells. The inventors' initial efforts were focused on the screening for miRNAs that promote cardiac myocyte formation in ES cells. Lentiviral vectors encoding miRNAs were introduced into E14 ES cells. At day 5 of the standard EB culture protocol, the cells were loaded with Fluo-4, and pulsed with a micro-electrode. Calcium spikes were recorded as waves of Fluo-4 fluorescent signals. Early excitability is only observed in cells harboring certain miRNAs, and these cells often spontaneously beat after 2 more days of culture. Of the 20 miRNAs screened so far, miR322/503, miR-542 and miR-18 induced early excitability, a sign of early cardiomyocytes.

miR-322/503 Drive Precocious Cardiac Differentiation from ES Cells.

The miR-322/503 cluster has drawn the inventors' interest because it is the most enriched miRNA cluster in Mesp1-lineage cells, and it drives cardiac differentiation most effectively in the initial screening. Both miR-322 and miR-503 have a transient expression pattern during ES cell differentiation, with a peak around day 4, which mimics the expression pattern of Mesp1 (FIG. 3A). The inventors thus subcloned the cluster into a tet-on lentiviral vector pLVX-tight-puro (Clontech) and introduced the vector into E14 ES cells. In the presence of doxycycline, both miR-322 and miR-503 were highly induced (FIG. 3B). Of the many conditions the inventors have tried, inducing miR-322/503 by doxycycline at day 3.5-4 of EB culture, which simulates the endogenous expression of these miRNAs, was most effective in driving ES cells to the cardiac fate. Spontaneous beating can be observed in dox-supplemented culture as early day 6, but not in culture without dox. Also, in dox-supplemented cultures, the expression of cardiac genes, and staining of alpha sarcomeric actinin, are greatly augmented, especially in the earlier time points (FIGS. 3C-D).

miR-322/503 Determines Cell Fate by Inhibiting Key Targets.

Celf1 is mRNA alternative splicing factor (Dasgupta and Ladd, 2012). It is a predicted target of miR-322/503, which was biochemically verified elsewhere (Cui et al., 2012). In the inventors' hands, transfected miR-322/503 inhibited Celf1 protein expression, in a dose dependent manner. Strikingly, overexpression of Celf1 prevented ES cells to take the cardiomyocyte fate. By real time RT-PCR, miR-322 and miR-503 are mainly expressed in heart and skeletal muscle, while Celf1 is mainly expressed in the neural system (not shown). By in situ hybridization test on E7.5~E10.5 embryos, Celf1 is initially expressed in the primitive streak and then mainly enriched in the neural system (not shown). These results suggest that miR-322/503 determines cell fate by inhibiting other key cell fate regulators in both cardiac and skeletal muscle.

Summary

The inventors have identified a novel regulator of early cardiac fate, miR-322/503. It is most enriched in the earliest cardiac progenitors, and was the most potent in inducing cardiomyocyte formation in a screening assay. When induced to mimic its natural course in ES cells, it induced a precocious cardiac program. It is important to identify key targets of miR-322(424)/503 to understand further about early cardiac specification, and it is highly valuable to test if miR-322(424)/503 induces progenitor cell differentiation and help to restore cardiac function after ischemic heart injury.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. References

The following references, to the extent that they provide exemplary procedural or other details supplementary to those set forth herein, are specifically incorporated herein by reference.

Angel et al., *Cell*, 49:729, 1987b.
Angel et al., *Mol. Cell. Biol.*, 7:2256, 1987a.
Baichwal and Sugden, In: *Gene Transfer*, Kucherlapati (Ed), NY, Plenum Press, 117-148, 1986.
Banerji et al., *Cell*, 27(2 Pt 1):299-308, 1981.
Banerji et al., *Cell*, 33(3):729-740, 1983.
Barnes et al., *J. Biol. Chem.*, 272(17):11510-7, 1997.
Benvenisty and Neshif, *Proc. Natl. Acad. Sci. USA*, 83:9551-9555, 1986.
Berkhout et al., *Cell*, 59:273-282, 1989.
Bhaysar et al., *Genomics*, 35(1):11-23, 1996.
Blanar et al., *EMBO J.*, 8:1139, 1989.
Boshart et al., *Cell*, 41:521, 1985.
Bosze et al., *EMBO J.* 5(7):1615-1623, 1986.
Braddock et al., *Cell*, 58:269, 1989.
Campbell et al., *J. Mol. Biol.*, 180:1-19, 1984.
Campo et al., *Nature*, 303:77, 1983.
Celander et al., *J. Virology*, 62:1314, 1988.
Chandler et al., *Cell*, 33:489, 1983.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7:2745-2752, 1987.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Cui et al., *Mol Biol Cell*, 23(1): p. 151-62, 2012.
Dandolo et al., *J. Virology*, 47:55-64, 1983.
Dasgupta and Ladd, *Wiley Interdiscip Rev RNA*, 3(1): p. 104-21, 2012.
De Villiers et al., *Nature*, 312(5991):242-246, 1984.
Deschamps et al., *Science*, 230:1174-1177, 1985.
Dubensky et al., *Proc. Natl. Acad. Sci. USA*, 81:7529-7533, 1984.
Edbrooke et al., *Mol. Cell. Biol.*, 9:1908, 1989.
Edlund et al., *Science*, 230:912-916, 1985.
Fechheimer et al., *Proc Natl. Acad. Sci. USA*, 84:8463-8467, 1987.
Ferkol et al., *FASEB J.*, 7:1081-1091, 1993.
Fraley et al., *Proc Natl. Acad. Sci. USA*, 76:3348-3352, 1979
Franz et al., *Cardoscience*, 5(4):235-43, 1994.
Friedmann, *Science*, 244:1275-1281, 1989.
Fujita et al., *Cell*, 49:357, 1987.
Gamez, B., et al., *J Biol Chem*, 288(20): p. 14264-75, 2013.
Garbern and Lee, *Cell Stem Cell*, 12(6): p. 689-98, 2013.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.*, 6:1733-1739, 1987.
Gilles et al., *Cell*, 33:717, 1983.
Gloss et al., *EMBO J.*, 6:3735, 1987.
Godbout et al., *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Gopal-Srivastava et al., *J. Mol. Cell. Biol.*, 15(12):7081-90, 1995.
Graham and Prevec, In: *Methods in Molecular Biology: Gene Transfer and Expression Protocol*, Murray (Ed.), Humana Press, Clifton, N.J., 7:109-128, 1991.
Graham and van der Eb, *Virology*, 52:456-467, 1973.
Graham et al., *J. Gen. Virol.*, 36:59-72, 1977.
Greene et al., *Immunology Today*, 10:272, 1989
Grunhaus and Horwitz, *Seminar in Virology*, 3:237-252, 1992.
Harland and Weintraub, *J. Cell Biol.*, 101:1094-1099, 1985.
Hen et al., *Nature*, 321:249, 1986.
Hensel et al., *Lymphokine Res.*, 8:347, 1989.
Hermonat and Muzycska, *Proc. Nat'l Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Nat'l. Acad. Sci. USA* 90:2812-2816, 1993.
Hirochika et al., *J. Virol.*, 61:2599, 1987.
Holbrook et al., *Virology*, 157:211, 1987.
Horwich et al., *J. Virol.*, 64:642-650, 1990.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imler et al., *Mol. Cell. Biol.*, 7:2558, 1987.
Jakobovits et al., *Mol. Cell. Biol.*, 8:2555, 1988.
Jaynes et al., *Mol. Cell. Biol.*, 8:62, 1988.
Johnson et al., *Mol. Cell. Biol.*, 9:3393, 1989.
Jones and Shenk, *Cell*, 13:181-188, 1978.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Karlsson et al., *EMBO J.*, 5:2377-2385, 1986.
Katinka et al., *Cell*, 20:393, 1980.
Kato et al., *J. Biol Chem.*, 266(6):3361-3364, 1991.
Kawamoto et al., *Mol. Cell. Biol.*, 8:267, 1988.
Kelly et al., *J. Cell Biol.*, 129(2):383-96, 1995.
Kiledjian et al., *Mol. Cell. Biol.*, 8:145, 1988.
Kimura et al., *Dev. Growth Differ.*, 39(3):257-65, 1997.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
LaPointe et al., *J. Biol. Chem.*, 263(19):9075-8, 1988.
Larsen et al., *Proc. Natl. Acad. Sci. USA.*, 83:8283, 1986.
Laspia et al., *Cell*, 59:283, 1989.
Latimer et al., *Mol. Cell. Biol.*, 10:760, 1990.
Le Gal La Salle et al., *Science*, 259:988-990, 1993.
Lee et al., *Nature*, 294:228, 1981.

Lee et al., *Nucleic Acids Res.*, 12:4191-206, 1984.
Levinson et al., *Nature*, 295:79, 1982.
Levrero et al., *Gene*, 101:195-202, 1991.
Li et al., *J. Biol. Chem.*, 271:19402-8, 1996.
Liu et al., *Genes Dev*, 22(23): p. 3242-54, 2008.
Liu et al., *Proc Natl Acad Sci USA*, 104(52): p. 20844-9, 2007.
Lin et al., *Mol. Cell. Biol.*, 10:850, 1990.
Luria et al., *EMBO J.*, 6:3307, 1987.
Lusky et al., *Mol. Cell. Biol.*, 3:1108, 1983.
Macejak and Sarnow, *Nature*, 353:90-94, 1991.
Mann et al., *Cell*, 33:153-159, 1983.
Markowitz et al., *J. Virol.*, 62:1120-1124, 1988.
McNeall et al., *Gene*, 76:81, 1989.
Miksicek et al., *Cell*, 46:203, 1986.
Moreau et al., *Nucl. Acids Res.*, 9:6047, 1981.
Moss et al., *J. Gen. Physiol.*, 108(6):473-84, 1996.
Muesing et al., *Cell*, 48:691, 1987.
Ng et al., *Nuc. Acids Res.*, 17:601, 1989.
Nicolas and Rubinstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Ondek et al., *EMBO J.*, 6:1017, 1987.
Ornitz et al., *Mol. Cell. Biol.*, 7:3466, 1987.
Palmiter et al., *Cell*, 29:701, 1982.
Palmiter et al., *Nature*, 300:611, 1982.
Paskind et al., *Virology*, 67:242-248, 1975.
Pech et al., *Mot. Cell. Biol.*, 9:396, 1989.
Pelletier and Sonenberg, *Nature*, 334:320-325, 1988.
Perales et al., *Proc. Natl. Acad. Sci. USA*, 91(9):4086-4090, 1994.
Perez-Stable and Constantini, *Mol. Cell. Biol.*, 10:1116, 1990.
Physicians Desk Reference.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porter and Turner, *Pharmacol. Ther.*, 123:255-278, 2009.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Qian et al., *Nature*, 485(7400): p. 593-8, 2012.
Quinn et al., *Mol. Cell. Biol.*, 9:4713, 1989.
Racher et al., *Biotech. Techniques*, 9:169-174, 1995.
Ragot et al., *Nature*, 361:647-650, 1993.
Redondo et al., *Science*, 247:1225, 1990.
Reinhold-Hurek and Shub, *Nature*, 357:173-176, 1992.
Reisman and Rotter, *Mol. Cell. Biol.*, 9:3571, 1989.
Remington's Pharmaceutical Sciences, 15$^{th}$ ed., 1035-1038 and 1570-1580, Mack Publishing Company, PA, 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A survey of molecular cloning vectors and their uses*, Stoneham: Butterworth, 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rosen et al., *Cell*, 41:813, 1988.
Rosenfeld et al., *Cell*, 68:143-155, 1992.
Rosenfeld et al., *Science*, 252:431-434, 1991.
Roux et al., *Proc. Natl. Acad. Sci. USA*, 86:9079-9083, 1989.
Russell et al., *Biochim. Biophys. Acta*, 1443(3):393-399, 1999.
Russell et al., *Circ Res.*, 108:51-59, 2011.
Saga et al., *Trends Cardiovasc Med*, 10(8): p. 345-52, 2000.
Saga et al., *Development*, 126(15): p. 3437-47, 1999.
Sakai et al., *Genes and Dev.*, 2:1144, 1988.
Sarkar et al., *Mol Biol Cell*, 21(13): p. 2138-49, 2010.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp, *Genes Dev.*, 13:139-141, 1999.
Sherman et al., *Mol. Cell. Biol.*, 9:50, 1989.
Soifer et al. *Mol Ther*, 15(12): p. 2070-9, 2007.
Song et al., *Nature*, 485(7400): p. 599-604, 2012.
Spalholz et al., *Cell*, 42:183, 1985.
Stephens and Hentschel, *Biochem.* 1, 248:1, 1987.
Stratford-Perricaudet and Perricaudet, In: *Human Gene Transfer*, Cohen-Haguenauer and Boiron (Eds.), John Libbey Eurotext, France, 51-61, 1991.
Stratford-Perricaudet et al., *Hum. Gene. Ther.*, 1:241-256, 1990.
Stuart et al., *Nature*, 317:828, 1985.
Takebe et al., *Mol. Cell. Biol.*, 8:466, 1988.
Tavernier et al., *Nature*, 301:634, 1983.
Taylor et al., *J. Biol. Chem.*, 264:15160, 1989.
Temin, In: *Gene Transfer*, Kucherlapati (Ed.), NY, Plenum Press, 149-188, 1986.
Thiesen et al., *J. Virology*, 62:614, 1988.
Top et al., *J. Infect. Dis.*, 124:155-160, 1971.
Tronche et al., *Mol. Biol. Med.*, 7:173, 1990.
Tur-Kaspa et al., *Mol. Cell Biol.*, 6:716-718, 1986.
Tyndell et al., *Nuc. Acids. Res.*, 9:6231, 1981.
van Rooij et al., *Dev Cell*, 17(5): p. 662-73, 2009.
van Rooij et al., *Science*, 316(5824): p. 575-9, 2007.
Varmus et al., *Cell*, 25:23-36, 1981.
Vasseur et al., *Proc Natl. Acad. Sci. U.S.A.*, 77:1068, 1980.
Wagner et al., *Proc. Natl. Acad. Sci. USA*, 87(9):3410-3414, 1990.
Weber et al., *Cell*, 36:983, 1984.
Weinberger et al. *Mol. Cell. Biol.*, 8:988, 1984.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu, *Cell Stem Cell*, 3:1-2, 2008.
Xin et al., *Genes Dev*, 23(18): p. 2166-78, 2009.
Yamauchi-Takihara et al., *Proc. Natl. Acad. Sci. USA*, 86(10):3504-3508, 1989.
Yang et al., *Proc. Natl. Acad. Sci. USA*, 87:9568-9572, 1990.
Yang et al., *Nat Med*, 13(4): p. 486-91, 2007.
Young et al., In: *Handbook of Applied Therapeutics*, 7.1-7.12 and 9.1-9.10, 1989.
Yutzey et al. *Mol. Cell. Biol.*, 9:1397, 1989.
Zelenin et al., *FEBS Lett.*, 280:94-96, 1991.
Ziober and Kramer, *J. Bio. Chem.*, 271(37):22915-22922, 1996.

What is claimed is:

1. A method of treating a subject having suffered a myocardial infarct (MI) comprising administering to said subject miR-322 and/or miR-503, as well pri-miRNAs and pre-miRNAs thereof, wherein said administration of said miR-322- and/or miR-503, as well pri-miRNAs and pre-miRNAs thereof results in treatment of said subject for one or more symptoms of myocardial infarction.

2. The method of claim 1, wherein miR-322 and/or miR-503 is administered in a lipid delivery vehicle.

3. The method of claim 1, wherein miR-322 and/or miR-503 is administered in a nanoparticle.

4. The method of claim 1, wherein administering comprises delivering an miR-322 and/or miR-503 expression cassette to said cell.

5. The method of claim 4, wherein said expression cassette is comprised in a replicable vector.

6. The method of claim 5, wherein said replicable vector is a viral vector.

7. The method of claim 6, wherein said viral vector is an adenoviral vector or retroviral vector.

8. The method of claim 5, wherein said replicable vector is a non-viral vector.

9. The method of claim 8, wherein said non-viral vector is disposed in a lipid delivery vehicle.

10. The method of claim 8, wherein said non-viral vector is disposed in or on a nanoparticle.

11. The method of claim 4, wherein said expression cassette comprises a global promoter, a cardiac mesoderm promoter or a cardiomyocyte promoter.

12. The method of claim 1, wherein miR-322 and/or miR-503 is administered more than once.

13. The method of claim 12, wherein the expression cassette is delivered 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times.

14. The method of claim 12, wherein the expression cassette is delivered daily.

15. The method of claim 1, miR-322 and/or miR-503 is delivered intracardiac injection.

16. The method of claim 1, wherein said subject is further administered oxygen, aspirin, and or nitroglycerin.

17. The method of claim 1, wherein said subject is further administered percutaneous coronary intervention or a fibrinolytic.

18. The method of claim 1, wherein said miR-322 and/or miR-503 are targeted to a residential embryonic stem cell or a residential cardiac progenitor cell.

19. The method of claim 1, wherein treating comprises reducing hospitalization, preventing or delaying development of cardiac hypertrophy, reducing decrease in exercise tolerance, improving quality of life, decreasing morbidity or decreasing mortality of said subject.

\* \* \* \* \*

SEQUENCE LISTING

```
<160> NUMBER OF SEQ ID NOS: 21

<210> SEQ ID NO 1
<211> LENGTH: 22
<212> TYPE: RNA
<213> ORGANISM: Homo sapiens

<400> SEQUENCE: 1
cagcagcaau ucauguuuug ga                                              22

<210> SEQ ID NO 2
<211> LENGTH: 22
<212> TYPE: RNA
<213> ORGANISM: Homo sapiens

<400> SEQUENCE: 2
cagcagcaau ucauguuuug aa                                              22

<210> SEQ ID NO 3
<211> LENGTH: 23
<212> TYPE: RNA
<213> ORGANISM: Homo sapiens

<400> SEQUENCE: 3
uagcagcggg aacaguucug cag                                             23

<210> SEQ ID NO 4
<211> LENGTH: 22
<212> TYPE: RNA
<213> ORGANISM: Rattus norvegicus

<400> SEQUENCE: 4
cagcagcaau ucauguuuug ga                                              22

<210> SEQ ID NO 5
<211> LENGTH: 21
<212> TYPE: RNA
<213> ORGANISM: Cricetulus griseus

<400> SEQUENCE: 5
cagcagcaau ucauguuuug g                                               21

<210> SEQ ID NO 6
<211> LENGTH: 22
<212> TYPE: RNA
<213> ORGANISM: Macaca mulatta

<400> SEQUENCE: 6
cagcagcaau ucauguuuug aa                                              22

<210> SEQ ID NO 7
<211> LENGTH: 22
<212> TYPE: RNA
<213> ORGANISM: Pan troglodytes

<400> SEQUENCE: 7
cagcagcaau ucauguuuug aa                                              22

<210> SEQ ID NO 8
<211> LENGTH: 21
<212> TYPE: RNA
<213> ORGANISM: Bos Taurus

<400> SEQUENCE: 8
```

-continued

```
cagcagcaau ucauguuug a                                               21

<210> SEQ ID NO 9
<211> LENGTH: 22
<212> TYPE: RNA
<213> ORGANISM: Equus caballus

<400> SEQUENCE: 9
cagcagcaau ucauguuug aa                                              22

<210> SEQ ID NO 10
<211> LENGTH: 22
<212> TYPE: RNA
<213> ORGANISM: Pongo pygmaeus

<400> SEQUENCE: 10
cagcagcaau ucauguuug aa                                              22

<210> SEQ ID NO 11
<211> LENGTH: 21
<212> TYPE: RNA
<213> ORGANISM: Gorilla gorilla

<400> SEQUENCE: 11
cagcagcaau ucauguuug a                                               21

<210> SEQ ID NO 12
<211> LENGTH: 23
<212> TYPE: RNA
<213> ORGANISM: Mus musculus

<400> SEQUENCE: 12
uagcagcggg aacaguacug cag                                            23

<210> SEQ ID NO 13
<211> LENGTH: 23
<212> TYPE: RNA
<213> ORGANISM: Rattus norvegicus

<400> SEQUENCE: 13
uagcagcggg aacaguacug cag                                            23

<210> SEQ ID NO 14
<211> LENGTH: 23
<212> TYPE: RNA
<213> ORGANISM: Macaca mulatta

<400> SEQUENCE: 14
uagcagcggg aacaguucug cag                                            23

<210> SEQ ID NO 15
<211> LENGTH: 20
<212> TYPE: RNA
<213> ORGANISM: Canis familiaris

<400> SEQUENCE: 15
uagcagcggg aacaguacug                                                20

<210> SEQ ID NO 16
<211> LENGTH: 23
<212> TYPE: RNA
<213> ORGANISM: Pan troglodytes
```

```
<400> SEQUENCE: 16
uagcagcggg aacaguucug cag                                            23

<210> SEQ ID NO 17
<211> LENGTH: 23
<212> TYPE: RNA
<213> ORGANISM: Sus scrofa

<400> SEQUENCE: 17
uagcagcggg aacaguacug cag                                            23

<210> SEQ ID NO 18
<211> LENGTH: 23
<212> TYPE: RNA
<213> ORGANISM: Equus caballus

<400> SEQUENCE: 18
uagcagcggg aacaguacug cag                                            23

<210> SEQ ID NO 19
<211> LENGTH: 23
<212> TYPE: RNA
<213> ORGANISM: Pongo pygmaeus

<400> SEQUENCE: 19
uagcagcggg aacaguucug cag                                            23

<210> SEQ ID NO 20
<211> LENGTH: 23
<212> TYPE: RNA
<213> ORGANISM: Gorilla gorilla

<400> SEQUENCE: 20
uagcagcggg aacaguucug cag                                            23

<210> SEQ ID NO 21
<211> LENGTH: 20
<212> TYPE: RNA
<213> ORGANISM: Bos Taurus

<400> SEQUENCE: 21
uagcagcggg aacaguacug                                                20
```